(12) United States Patent
Bruker et al.

(10) Patent No.: US 10,278,692 B2
(45) Date of Patent: May 7, 2019

(54) SLING SUSPENSION SYSTEM FOR SUPPORTING THE THUMB OF A PATIENT AFTER BASAL JOINT ARTHROPLASTY

(71) Applicant: CMC Group LLC, Newton, MA (US)

(72) Inventors: Izi Bruker, Newton, MA (US); Jeanne L. DelSignore, Rochester, NY (US); Kevin L. Ohashi, Jamaica Plains, MA (US); James Christopher Harber, Shorewood, MN (US)

(73) Assignee: CMC Group LLC, Newton, MA (US)

( * ) Notice: Subject to any disclaimer, the term of this patent is extended or adjusted under 35 U.S.C. 154(b) by 0 days.

(21) Appl. No.: 14/596,973

(22) Filed: Jan. 14, 2015

(65) Prior Publication Data

US 2015/0127047 A1    May 7, 2015

Related U.S. Application Data (63) Continuation-in-part of application No. 12/577,057, filed on Oct. 9, 2009, now abandoned.
(Continued)

(51) Int. Cl.
| A61B 17/06 | (2006.01) |
| A61B 17/04 | (2006.01) |
(Continued)

(52) U.S. Cl.
CPC .... A61B 17/06166 (2013.01); A61B 17/0401 (2013.01); A61B 17/68 (2013.01);
(Continued)

(58) Field of Classification Search
CPC ........ A61B 17/0401; A61B 2017/0414; A61B 2017/0427; A61B 2017/044;
(Continued)

(56) References Cited

U.S. PATENT DOCUMENTS

| 2,416,260 A | 2/1947 | Karle |
| 2,579,192 A | 8/1951 | Kohl et al. |

(Continued)

FOREIGN PATENT DOCUMENTS

| WO | WO 2006/034719 | 4/2006 |
| WO | WO 2007/002071 | 1/2007 |
| WO | WO 2010/047981 | 4/2010 |

OTHER PUBLICATIONS

Badia, Alejandro, Surgical Options for Thumb Basal Joint Arthritis, US Musculoskeletal Review, 2006, pp. 69-70.
(Continued)

*Primary Examiner* — Alexander J Orkin
(74) *Attorney, Agent, or Firm* — Pandiscio & Pandiscio (57) ABSTRACT

A sling suspension system for supporting the thumb of a patient after basal joint arthroplasty, the sling suspension system comprising: an index metacarpal anchor, a thumb metacarpal anchor and a sling for securing the thumb metacarpal anchor to the index metacarpal anchor; the index metacarpal anchor comprising at least one bone-engaging element for engaging the index metacarpal and a sling-engaging element for capturing the sling to the index metacarpal anchor; the thumb metacarpal anchor comprising at least one bone-engaging element for engaging the thumb metacarpal and a sling-engaging element for capturing the sling to the thumb metacarpal anchor; and the sling comprising an elongated body having a first anchor-engaging element for securing the sling to the sling-engaging element of the index metacarpal anchor, and a second anchor-engaging element for securing the sling to the sling-engaging element of the thumb metacarpal anchor, wherein the second anchor-engaging element is adjustable.

26 Claims, 5 Drawing Sheets

Related U.S. Application Data (60) Provisional application No. 61/197,060, filed on Oct. 23, 2008, provisional application No. 61/927,309, filed on Jan. 14, 2014.

(51) Int. Cl.
  *A61F 2/08* (2006.01)
  *A61B 17/68* (2006.01)
  *A61F 2/42* (2006.01)

(52) U.S. Cl.
  CPC ....... *A61F 2/0811* (2013.01); *A61B 2017/044* (2013.01); *A61B 2017/0414* (2013.01); *A61B 2017/0427* (2013.01); *A61B 2017/06185* (2013.01); *A61F 2/0805* (2013.01); *A61F 2/4241* (2013.01); *A61F 2002/087* (2013.01); *A61F 2002/0829* (2013.01); *A61F 2002/0858* (2013.01); *A61F 2002/0888* (2013.01); *A61F 2002/4253* (2013.01); *A61F 2250/0007* (2013.01)

(58) Field of Classification Search
  CPC ...... A61F 2002/4251; A61F 2002/4253; A61F 2002/0858
  See application file for complete search history.

(56) References Cited

U.S. PATENT DOCUMENTS

| | | |
|---|---|---|
| 2,808,055 A | 10/1957 | Thayer |
| 3,496,940 A | 2/1970 | Steinman |
| 3,545,008 A | 12/1970 | Bader, Jr. |
| 3,745,590 A * | 7/1973 | Stubstad ............ A61F 2/4241 128/DIG. 21 |
| 3,805,300 A | 4/1974 | Tascon-Alonso et al. |
| 4,187,558 A | 2/1980 | Dahlen et al. |
| 4,408,938 A | 10/1983 | Maguire |
| 4,484,570 A | 11/1984 | Sutter et al. |
| 4,492,226 A | 1/1985 | Belykh et al. |
| 4,590,928 A | 5/1986 | Hunt et al. |
| 4,713,075 A | 12/1987 | Kurland |
| 4,741,330 A | 5/1988 | Hayhurst |
| 4,775,380 A | 10/1988 | Seedhom et al. |
| 4,778,468 A | 10/1988 | Hunt et al. |
| 4,779,616 A | 10/1988 | Johnson |
| 4,870,957 A | 10/1989 | Goble et al. |
| 4,871,289 A | 10/1989 | Choiniere |
| 4,927,421 A | 5/1990 | Goble et al. |
| 5,037,422 A | 8/1991 | Hayhurst et al. |
| 5,046,513 A | 9/1991 | Gatturna et al. |
| 5,207,679 A | 5/1993 | Li |
| 5,209,753 A | 5/1993 | Biedermann et al. |
| 5,224,946 A | 7/1993 | Hayhurst et al. |
| 5,226,426 A | 7/1993 | Yoon |
| 5,236,445 A | 8/1993 | Hayhurst et al. |
| 5,268,001 A | 12/1993 | Nicholson et al. |
| 5,324,308 A | 6/1994 | Pierce |
| 5,336,240 A | 8/1994 | Metzler et al. |
| 5,354,298 A | 10/1994 | Lee et al. |
| 5,417,712 A | 5/1995 | Whittaker et al. |
| 5,423,860 A | 6/1995 | Lizardi et al. |
| 5,464,427 A | 11/1995 | Curtis et al. |
| 5,480,403 A | 1/1996 | Lee et al. |
| 5,486,197 A | 1/1996 | Le et al. |
| 5,501,695 A | 3/1996 | Anspach, Jr. et al. |
| 5,522,844 A | 6/1996 | Johnson |
| 5,522,845 A | 6/1996 | Wenstrom, Jr. |
| 5,534,012 A | 7/1996 | Bonutti |
| 5,545,180 A | 8/1996 | Le et al. |
| 5,569,306 A | 10/1996 | Thal |
| 5,584,835 A | 12/1996 | Greenfield |
| 5,601,558 A | 2/1997 | Torrie et al. |
| 5,611,515 A | 3/1997 | Benderev et al. |
| 5,632,748 A | 5/1997 | Beck, Jr. et al. |
| 5,643,321 A | 7/1997 | McDevitt |
| 5,645,589 A | 7/1997 | Li |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,681,320 A | 10/1997 | McGuire |
| 5,683,419 A | 11/1997 | Thal |
| 5,690,649 A | 11/1997 | Li |
| 5,702,215 A | 12/1997 | Li |
| 5,702,397 A | 12/1997 | Goble et al. |
| 5,702,422 A | 12/1997 | Stone |
| 5,702,468 A * | 12/1997 | Goldberg ............... A61F 2/4225 623/21.12 |
| 5,707,395 A | 1/1998 | Li |
| 5,709,708 A | 1/1998 | Thal |
| 5,716,368 A | 2/1998 | de la Torre et al. |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,741,301 A | 4/1998 | Pagedas |
| 5,782,863 A | 7/1998 | Bartlett |
| 5,782,864 A | 7/1998 | Lizardi |
| 5,797,963 A | 8/1998 | McDevitt |
| 5,814,071 A | 9/1998 | McDevitt et al. |
| 5,814,072 A | 9/1998 | Bonutti |
| 5,814,073 A | 9/1998 | Bonutti |
| 5,843,127 A | 12/1998 | Li |
| 5,845,645 A | 12/1998 | Bonutti |
| 5,849,004 A | 12/1998 | Bramlet |
| 5,860,978 A * | 1/1999 | McDevitt ............... A01B 1/222 606/232 |
| 5,906,624 A | 5/1999 | Wenstrom, Jr. |
| 5,911,721 A | 6/1999 | Nicholson et al. |
| 5,928,244 A | 7/1999 | Tovey et al. |
| 5,935,129 A | 8/1999 | McDevitt et al. |
| 5,935,134 A | 8/1999 | Pedlick et al. |
| 5,957,953 A | 9/1999 | DiPoto et al. |
| 5,968,044 A | 10/1999 | Nicholson et al. |
| 5,980,558 A | 11/1999 | Wiley |
| 5,980,559 A | 11/1999 | Bonutti |
| 5,993,459 A | 11/1999 | Larsen et al. |
| 6,010,447 A | 1/2000 | Kardjian |
| 6,041,485 A | 3/2000 | Pedlick et al. |
| 6,042,534 A | 3/2000 | Gellman et al. |
| 6,045,573 A | 4/2000 | Wenstrom, Jr. et al. |
| 6,056,772 A | 5/2000 | Bonutti |
| 6,083,522 A * | 7/2000 | Chu .................. A61B 17/0401 424/423 |
| 6,086,608 A | 7/2000 | Ek et al. |
| 6,099,547 A | 8/2000 | Gellman et al. |
| 6,110,101 A | 8/2000 | Tihon et al. |
| 6,117,144 A | 9/2000 | Nobles et al. |
| 6,149,653 A * | 11/2000 | Deslauriers ........ A61B 17/0401 606/232 |
| 6,245,082 B1 | 6/2001 | Gellman et al. |
| 6,267,766 B1 * | 7/2001 | Burkhart ............ A61B 17/0401 606/232 |
| 6,312,448 B1 | 11/2001 | Bonutti |
| 6,319,269 B1 | 11/2001 | Li |
| 6,368,326 B1 * | 4/2002 | Dakin .................. A61B 17/683 606/103 |
| 6,506,190 B1 | 1/2003 | Walshe |
| 6,517,578 B2 | 2/2003 | Hein |
| 6,524,316 B1 | 2/2003 | Nicholson et al. |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,562,071 B2 | 5/2003 | Järvinen |
| 6,575,987 B2 | 6/2003 | Gellman et al. |
| 6,641,596 B1 | 11/2003 | Lizardi |
| 6,660,023 B2 | 12/2003 | McDevitt et al. |
| 6,673,094 B1 | 1/2004 | McDevitt et al. |
| 6,775,928 B2 | 8/2004 | Grande et al. |
| 6,872,227 B2 | 3/2005 | Sump et al. |
| 7,073,279 B2 | 7/2006 | Min |
| 7,083,568 B2 | 8/2006 | Neisz et al. |
| 7,938,847 B2 | 5/2011 | Fanton et al. |

(56) References Cited

U.S. PATENT DOCUMENTS

| | | |
|---|---|---|
| 8,398,678 B2 | 3/2013 | Baker et al. |
| 8,439,976 B2 | 5/2013 | Albertorio et al. |
| 8,460,319 B2 | 6/2013 | Wales et al. |
| 8,512,376 B2 | 8/2013 | Thornes |
| 8,721,650 B2 | 5/2014 | Fanton et al. |
| 8,753,375 B2 | 6/2014 | Albertorio |
| 8,758,406 B2 | 6/2014 | Fenton et al. |
| 8,888,815 B2 | 11/2014 | Holmes, Jr. |
| 9,023,083 B2 | 5/2015 | Foerster et al. |
| 9,179,950 B2 | 11/2015 | Zajac et al. |
| 9,707,090 B2 | 7/2017 | DelSignore |
| 2001/0008971 A1 | 7/2001 | Schwartz et al. |
| 2002/0019670 A1 | 2/2002 | Crawley et al. |
| 2002/0123750 A1 | 9/2002 | Eisermann et al. |
| 2003/0039676 A1* | 2/2003 | Boyce ............. A61B 17/0401 424/423 |
| 2003/0130694 A1* | 7/2003 | Bojarski ........... A61B 17/0401 606/228 |
| 2003/0139775 A1 | 7/2003 | Grafton |
| 2004/0127906 A1* | 7/2004 | Culbert ............ A61B 17/7064 606/247 |
| 2005/0019368 A1* | 1/2005 | Cook ............... A61B 17/0401 424/426 |
| 2005/0245932 A1 | 11/2005 | Fanton et al. |
| 2006/0149261 A1 | 7/2006 | Nilsson et al. |
| 2006/0195007 A1 | 8/2006 | Anderson et al. |
| 2006/0241617 A1 | 10/2006 | Holloway et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0255317 A1 | 11/2007 | Fanton et al. |
| 2007/0260259 A1 | 11/2007 | Fanton et al. |
| 2009/0018655 A1 | 1/2009 | Brunelle et al. |
| 2009/0171143 A1 | 7/2009 | Chu et al. |
| 2009/0254190 A1* | 10/2009 | Gannoe ............ A61B 17/0401 623/21.11 |
| 2009/0306776 A1 | 12/2009 | Murray |
| 2010/0106254 A1 | 4/2010 | Delsignore |
| 2011/0208239 A1 | 8/2011 | Stone et al. |
| 2011/0270306 A1 | 11/2011 | Denham et al. |
| 2013/0035720 A1 | 2/2013 | Perriello et al. |
| 2013/0172944 A1 | 7/2013 | Fritzinger et al. |
| 2013/0211451 A1 | 8/2013 | Wales et al. |
| 2014/0121682 A1 | 5/2014 | Ferree |
| 2014/0296911 A1 | 10/2014 | Fanton et al. |
| 2015/0032156 A1 | 1/2015 | Bennett |
| 2015/0127047 A1 | 5/2015 | Bruker et al. |
| 2015/0164498 A1 | 6/2015 | Dreyfuss et al. |
| 2016/0302786 A1 | 10/2016 | Bennett et al. |

OTHER PUBLICATIONS

Cassidy et al., Basal Joint Arthroplasty and Carpal Tunnel Release Through a Single Incision: An In Vitro Study, J. Hand Surg., vol. 29A, pp. 1085-1088.

Delsignore et al., Suture Suspension Arthroplasty Technique for Basal Joint Arthritis Reconstruction, Techniques in Hand and Upper Extremity, to be published, Dec. 2009.

Delsignore, Jeanne, A Modified Technique for Basal Joint Suspensionplasty, Am. Soc. Hand Surgery, Aug. 2004, Issue No. 52.

Glickel et al., Basal Joint Arthroplasty: Indications and Treatment; Current Opinion in Orthopaedics, 2001, vol. 12, pp. 290-292.

Griggs et al., The Use of Suture Anchors in the Hand and Wrist, in Current Practice in Hand Surgery, 1997; pp. 73-77, Mosby, St. Louis/USA.

Heyworth, Benton, Tendon Transfer Arthroplasty vs. LRTI Arthroplasty . . . , Doris Duke Medical Student's Journal, vol. II, 2002-2003, pp. 46-52.

Matullo et al., CMC Arthroplasty of the Thumb: A Review, Am. Assn. Hand Surgery, Aug. 7, 2007.

PCT Search Report for PCT Application No. PCT/US2009/060263; dated Dec. 1, 2009; 3 pages.

Shaieb et al., Tensile Strengths of Various Suture Techniques, J. Hand Surgery (British and European Volume, 1997), vol. 22B, pp. 764-767.

Shuler et al., Basal Joint Arthritis of the Thumb, J. Am. Acad. Orthop. Sug., 2008, vol. 16, pp. 418-423.

Weidrich et al., The Use of Suture Anchors in the Hand and Wrist, Operative Tech. In Plastic and Recon. Surg., 1997, vol. 4, pp. 42-48.

TORNIER, Piton product brochure. 2016.

Trumble et al., Thumb Carpometacarpal Arthroplasty with Ligament Reconstruction and Interposition Costochondral Arthroplasty, Journal of Wrist Surgery, 2013, vol. 2, No. 3, pp. 220-227.

* cited by examiner

SLING SUSPENSION SYSTEM FOR SUPPORTING THE THUMB OF A PATIENT AFTER BASAL JOINT ARTHROPLASTY

REFERENCE TO PENDING PRIOR PATENT APPLICATIONS

This patent application:

(i) is a continuation-in-part of pending prior U.S. patent application Ser. No. 12/577,057, filed Oct. 9, 2009 by Jeanne L. DelSignore for SURGICAL IMPLANTABLE STABILIZER SLING FOR BASAL JOINT ARTHROPLASTY, which patent application claims benefit of prior U.S. Provisional Patent Application Ser. No. 61/197,060, filed Oct. 23, 2008 by Jeanne Louise DelSignore for SURGICAL IMPLANTABLE STABILIZER SLING FOR BASAL JOINT ARTHROPLASTY; and (ii) claims benefit of prior U.S. Provisional Patent Application Ser. No. 61/927,309, filed Jan. 14, 2014 by CMC Group LLC and Izi Bruker et al. for BASAL THUMB ARTHRITIS SLING SYSTEM.

The three (3) above-identified patent applications are hereby incorporated herein by reference.

FIELD OF THE INVENTION

This invention relates to surgical methods and apparatus in general, and more particularly to a novel sling suspension system for supporting the thumb of a patient after basal joint arthroplasty.

BACKGROUND OF THE INVENTION

Degenerative osteoarthritis of the first metacarpal joint of the thumb (sometimes referred to as "the basal joint") is a common debilitating condition, especially in middle aged women. Investigations show that 25% of all women and 8% of all men in their fifties complain of pain in the base of the thumb, secondary to basal joint osteoarthritis.

Basal joint arthritis can cause substantial pain, digit weakness and loss of functionality.

In severe cases of basal joint arthritis, basal joint reconstruction may be required. In general, basal joint reconstruction involves trapezial excision ("basal joint arthroplasty"), which is required for pain relief, and subsequent soft tissue reconstruction in order to re-create proper balance, alignment, longitudinal length and function to the thumb.

Unfortunately, this soft tissue reconstruction has historically involved harvesting tendons which are subsequently transferred and redirected via drill holes in the thumb metacarpal in order to restore proper balance, alignment, longitudinal length and function to the thumb. However, this means harvesting, and thereby sacrificing, all or some of a functioning tendon. In addition, the reconstruction typically requires temporary pinning, which can give rise to pin tract complications such as infection, nerve damage and neuroma formation.

As a result, a new approach is needed for effecting basal joint reconstruction after performing basal joint arthroplasty in order to alleviate basal joint arthritis.

SUMMARY OF THE INVENTION

The present invention provides a new approach for effecting basal joint reconstruction after performing basal joint arthroplasty in order to alleviate basal joint arthritis.

More particularly, the present invention comprises the provision and use of a novel sling suspension system that joins the thumb metacarpal to the index metacarpal so as to support the thumb of a patient after basal joint arthroplasty. The present invention eliminates the specific complications and increased morbidity associated with tendon harvesting and transfer procedures and those procedures that require temporary pin fixation or drill holes for tendon or suture passage. The novel sling suspension system of the present invention provides secure and stable support for the thumb of a patient after performing basal joint arthroplasty in order to alleviate basal joint arthritis, and is relatively fast and simple to implement.

In one preferred form of the present invention, there is provided a sling suspension system for supporting the thumb of a patient after basal joint arthroplasty, said sling suspension system comprising:

an index metacarpal anchor, a thumb metacarpal anchor and a sling for securing said thumb metacarpal anchor to said index metacarpal anchor;

said index metacarpal anchor comprising at least one bone-engaging element for engaging the index metacarpal and a sling-engaging element for capturing said sling to said index metacarpal anchor;

said thumb metacarpal anchor comprising at least one bone-engaging element for engaging the thumb metacarpal and a sling-engaging element for capturing said sling to said thumb metacarpal anchor; and said sling comprising an elongated body having a first anchor-engaging element for securing said sling to said sling-engaging element of said index metacarpal anchor, and a second anchor-engaging element for securing said sling to said sling-engaging element of said thumb metacarpal anchor, wherein said second anchor-engaging element is adjustable.

In another preferred form of the present invention, there is provided a method for supporting the thumb of a patient after basal joint arthroplasty, said method comprising:

securing a first end of a sling to an index metacarpal anchor;

positioning the index metacarpal anchor in the index metacarpal;

adjustably securing the second end of the sling to a thumb metacarpal anchor;

adjusting the securement of the second end of the sling to the thumb metacarpal anchor so that the thumb metacarpal anchor is brought adjacent to the thumb metacarpal; and inserting the thumb metacarpal anchor into the thumb metacarpal so that the second end of the sling is fixedly secured to the thumb metacarpal anchor, whereby the sling fixedly connects the thumb metacarpal to the index metacarpal.

In another preferred form of the present invention, there is provided a method for alleviating basal joint arthritis, said method comprising:

excising the trapezium of a patient; securing a first end of a sling to an index metacarpal anchor;

positioning the index metacarpal anchor in the index metacarpal;

adjustably securing the second end of the sling to a thumb metacarpal anchor;

adjusting the securement of the second end of the sling to the thumb metacarpal anchor so that the thumb metacarpal anchor is brought adjacent to the thumb metacarpal; and inserting the thumb metacarpal anchor into the thumb metacarpal so that the second end of the sling is fixedly secured to the thumb metacarpal anchor, whereby the sling fixedly connects the thumb metacarpal to the index metacarpal.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
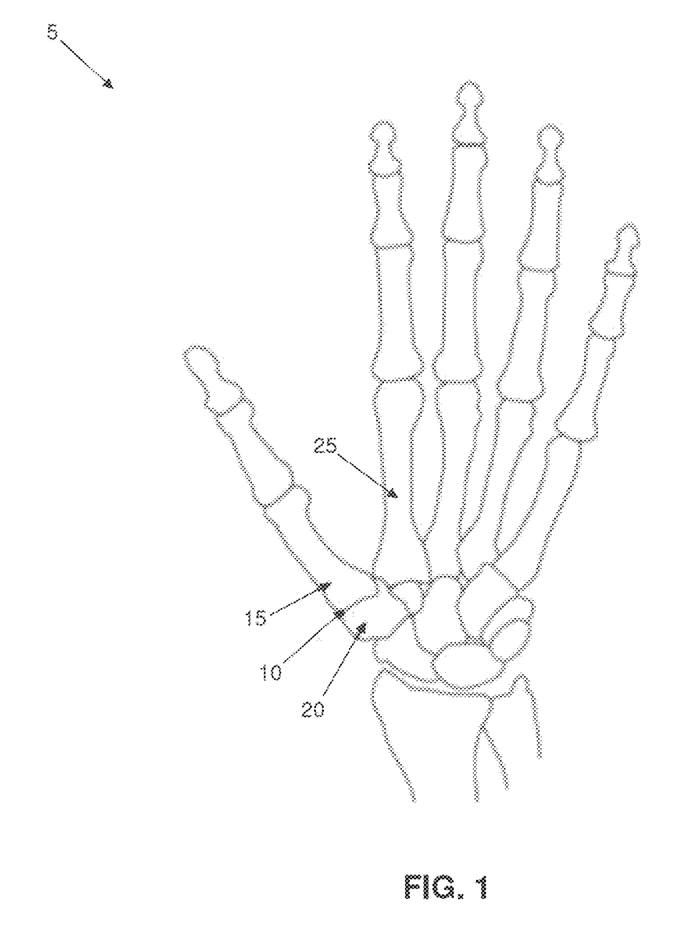
FIG. 1 is a schematic view showing the bone structure of the right hand of a human.

Looking first at FIG. 1, there is shown the right hand 5 of a human. As seen in the figure, the basal joint 10 is formed at the junction of the thumb metacarpal 15 and the trapezium 20. Note also the location of the adjacent index metacarpal 25.

As noted above, many people suffer from significant basal joint arthritis and would benefit from basal joint reconstruction in order to alleviate the basal joint arthritis.

The present invention provides a new approach for effecting basal joint reconstruction after performing basal joint arthroplasty in order to alleviate basal joint arthritis.

More particularly, the present invention comprises the provision and use of a novel sling suspension system that joins the thumb metacarpal to the index metacarpal so as to support the thumb of a patient after basal joint arthroplasty. The present invention eliminates the specific complications and increased morbidity associated with tendon harvesting and transfer procedures and those procedures that require temporary pin fixation or drill holes for tendon or suture passage. The novel sling suspension system of the present invention provides secure and stable support for the thumb of a patient after performing basal joint arthroplasty in order to alleviate basal joint arthritis, and is relatively fast and simple to implement.

The Novel Sling Suspension System

Figure 2:
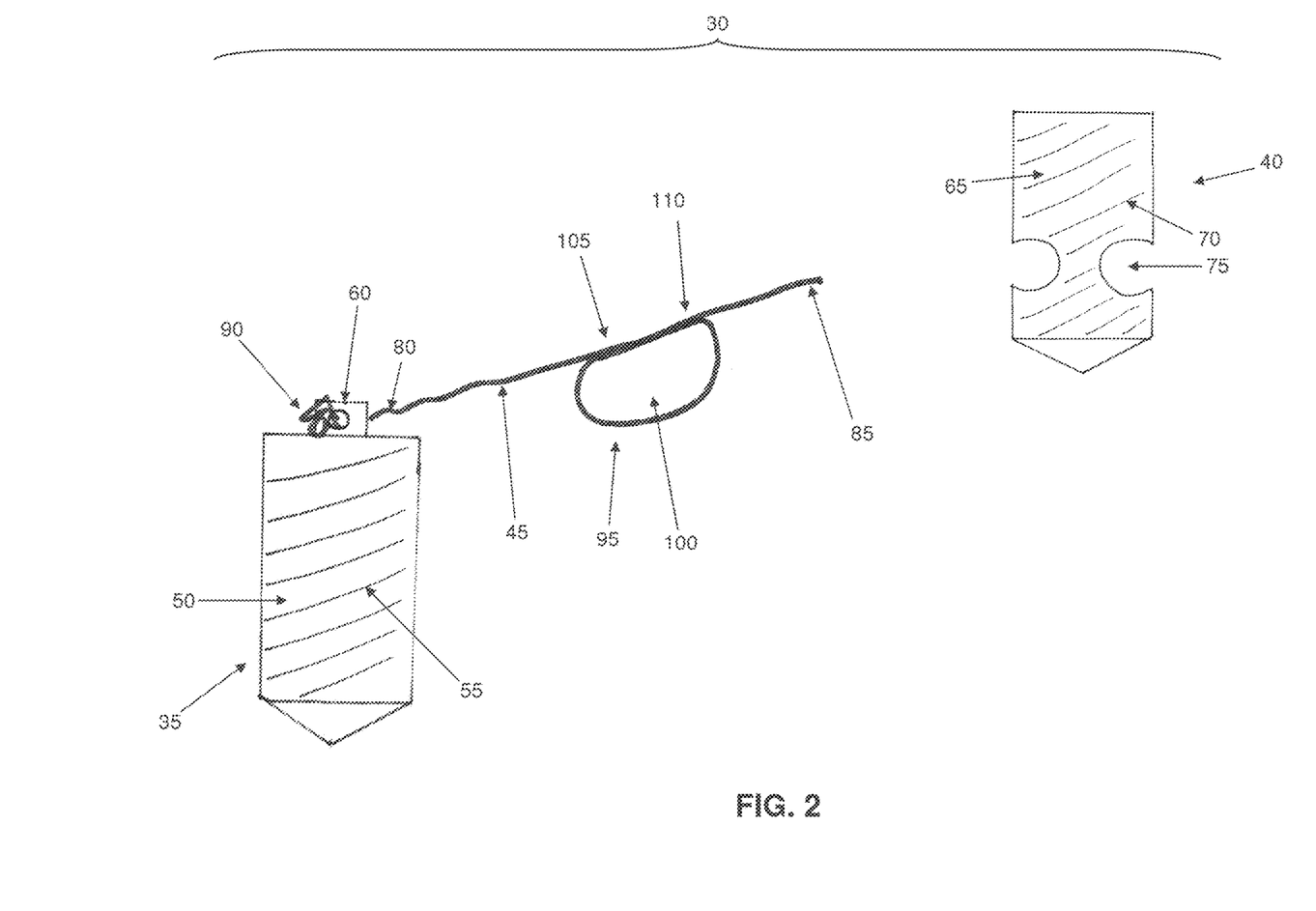
FIG. 2 is a schematic view of a novel sling suspension system formed in accordance with the present invention.

Looking next at FIG. 2, there is shown a novel sling suspension system 30 formed in accordance with the present invention. Sling suspension system 30 generally comprises an index metacarpal anchor 35 for deployment in index metacarpal 25, a thumb metacarpal anchor 40 for deployment in thumb metacarpal 15, and a sling 45 for securing thumb metacarpal anchor 40 to index metacarpal anchor 35, whereby to provide a sling suspension system for supporting the thumb of a patient after basal joint arthroplasty has been performed in order to alleviate basal joint arthritis.

Index metacarpal anchor 35 is intended to be deployed in (e.g., screwed into or pushed into) a drill hole formed at or near the base of index metacarpal 25. To this end, index metacarpal anchor 35 comprises a body 50 having at least one bone-engaging element 55 (e.g., screw threads, ribs, etc.) formed thereon for engaging index metacarpal 25. Index metacarpal anchor 35 further comprises a sling-engaging element 60 (e.g., an eyelet) for capturing sling 45 to index metacarpal anchor 35.

Thumb metacarpal anchor 40 is intended to be deployed in (e.g., screwed into or pushed into) a drill hole formed at or near the base of thumb metacarpal 15. To this end, thumb metacarpal anchor 40 comprises a body 65 having at least one bone-engaging element 70 (e.g., screw threads, ribs, etc.) formed thereon for engaging thumb metacarpal 15. Thumb metacarpal anchor 40 further comprises a sling-engaging element 75 (e.g., a groove or shoulder) for capturing sling 45 to thumb metacarpal anchor 40. In one form of the invention, sling-engaging element 75 (e.g., the groove or shoulder) traverses 360 degrees around body 65 of thumb metacarpal anchor 40.

Sling 45 secures thumb metacarpal anchor 40 to index metacarpal anchor 35, whereby to provide a sling suspension system for supporting the thumb of a patient after basal joint arthroplasty has been performed in order to alleviate basal joint arthritis. To this end, sling 45 comprise an elongated body having a first end 80 and a second end 85.

First end 80 includes an anchor-engaging element 90 (e.g., a knot) for securing sling 45 to sling-engaging element 60 of index metacarpal anchor 35 such that the sling is attached to the anchor.

Figure 3:
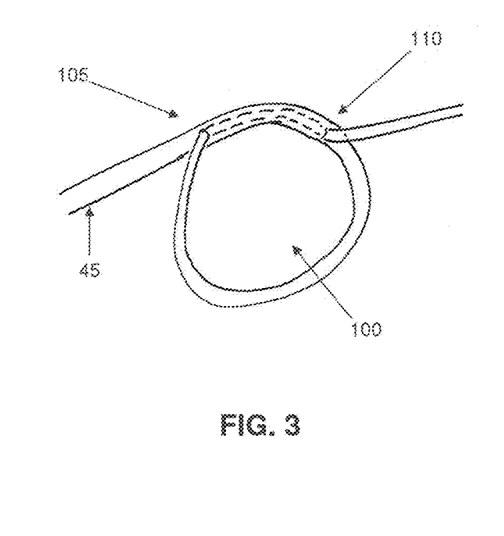
FIG. 3 is a schematic view showing an adjustable loop of the novel sling suspension system shown in FIG. 2.

Sling 45 also comprises an adjustable anchor-engaging element 95 for securing sling 45 to sling-engaging element 75 of thumb metacarpal anchor 40 such that the sling is attached to the anchor. In one preferred form of the invention, adjustable anchor-engaging element 95 comprises an adjustable loop 100 formed in sling 45 intermediate its first end 80 and its second end 85. As seen in FIG. 3, adjustable loop 100 is preferably formed by the sling being passed into itself at least once at a point 105 and emerging from itself at least once at a point 110. As a result of this construction, when first end 80 of sling 45 is held fixed (e.g., when first end 80 of sling 45 is secured to index metacarpal anchor 35 and index metacarpal anchor 35 is secured in index metacarpal 25), pulling on second end 85 of sling 45 will decrease the diameter of adjustable loop 100 (e.g., so as to secure sling 45 in groove 75 of thumb metacarpal anchor 40, whereby to secure sling 45 to thumb metacarpal anchor 40).

The elongated body of sling 45 may comprise a filament (e.g., a suture), a rope, a web, a tape, etc., i.e., substantially any elongated structure which will suffice for the intended purpose, either man-made or biologic (e.g., crosslinked collagen, crosslinked hydrogel, chitosan, etc.), as well as other biocompatible polymers or metals and/or composite structures. In one preferred form of the invention, sling 45 comprises a suture. It should be appreciated that sling 45 can be a hollow or solid core braided suture or a monofilament suture. It should also be appreciated that sling 45 should to be able to slide with respect to itself once it has been passed into itself, e.g., in the manner shown in FIG. 3. And it should be appreciated that sling 45 can be passed through itself in such a way that points 105 and 110 lie on the same plane perpendicular to the primary axis of the sling, or the planes of entry and exit (i.e., points 105 and 110) can be circumferentially offset from each other.

Note also that adjustable loop 100 may be formed without passing sling 45 back through itself, e.g., adjustable loop 45 may be formed by a sliding knot or any other construction that allows the size of adjustable loop 100 to be modified on demand.

If desired, multiple adjustable loops 100 may be provided along sling 45, whereby to allow one anchor to mate with multiple adjustable loops on sling 45, or to allow multiple anchors to mate with sling 45 (e.g., with each anchor engaging with one or more adjustable loops).

Figure 4:
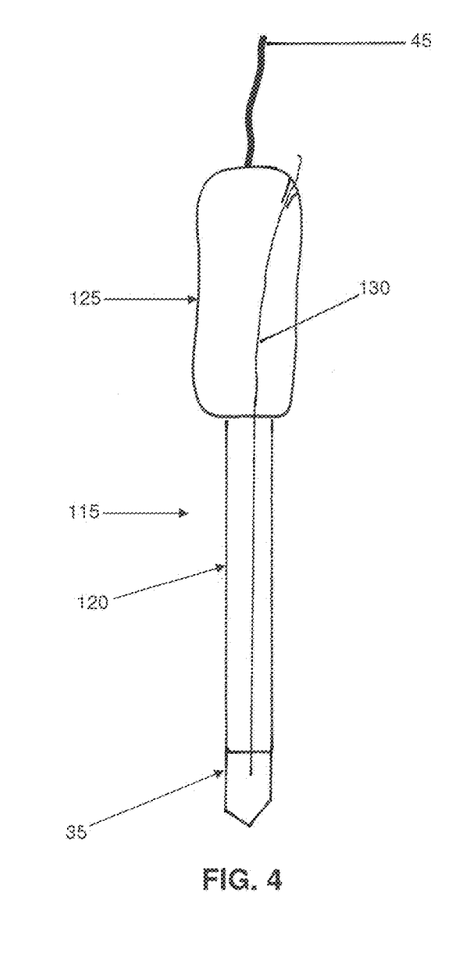
FIG. 4 is a schematic view showing the index metacarpal anchor and sling of the novel sling suspension system shown in FIG. 2 mounted to a driver.

Looking now at FIG. 4, sling suspension system 30 preferably also comprises a driver 115 which may be used to set index metacarpal anchor 35 into index metacarpal 25 and/or to set thumb metacarpal anchor 40 into thumb metacarpal 15. To this end, driver 115 comprises a shaft 120 having a drive feature at its distal end for engaging (i) a counterpart drive feature of index metacarpal anchor 35, so as to enable driver 115 to drive index metacarpal anchor 35 into index metacarpal 25, and/or (ii) a counterpart drive feature of thumb metacarpal anchor 40, so as to enable driver 115 to drive thumb metacarpal anchor 40 into thumb metacarpal 15. A handle 125 is provided at the proximal end of shaft 120.

In one preferred form of the invention, index metacarpal anchor 35 is pre-loaded on driver 115 at the time of system assembly and, after driver 115 has been used to set index metacarpal anchor 35 into index metacarpal 25, thumb metacarpal anchor 40 is loaded on driver 115 for setting thumb metacarpal anchor 40 into thumb metacarpal 15. Where index metacarpal anchor 35 is pre-loaded onto driver 115 at the time of system assembly, a stay line 130 can be used to secure index metacarpal anchor 35 onto driver 115. In one preferred form of the invention, driver 115 has a hollow construction such that sling 45 may be passed through shaft 120 and handle 130 of driver 115 and emerge at the proximal end of driver 115.

Use of the Novel Sling Suspension System

Sling suspension system 30 may be used in the following manner to support the thumb of a patient after basal joint arthroplasty has been performed in order to alleviate basal joint arthritis.

1. Trapezium 20 is excised so as to alleviate the basal joint arthritis. See FIG. 5.

Figure 5:
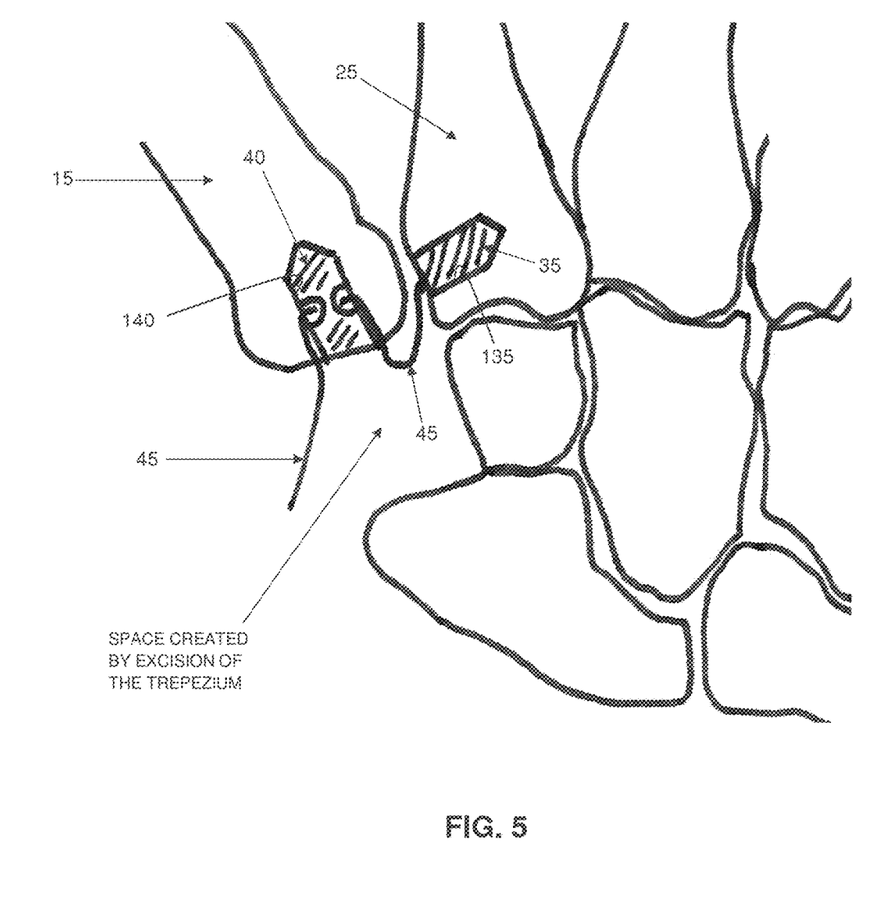
FIG. 5 is a schematic view showing a basal joint reconstruction using the novel sling suspension system shown in FIG. 2.

2. Index metacarpal 25 and thumb metacarpal 15 are prepared to receive index metacarpal anchor 35 and thumb metacarpal anchor 40, respectively. In one preferred form of the invention, a bone hole 135 is drilled into the thumb side of index metacarpal 25, and a bone hole 140 is drilled into the base of thumb metacarpal 15. Note that the space created by the excised trapezium allows easy access to the base of thumb metacarpal 15 and to index metacarpal 25.

3. First end 80 of sling 45 is attached to index metacarpal anchor 35 using sling-engaging element 60 of index metacarpal anchor 35 and anchor-engaging element 90 of sling 45 (e.g., eyelet 60 and knot 90), and index metacarpal anchor 35 and sling 45 are mounted to driver 115. Alternatively, and more preferably, first end 80 of sling 45 is pre-mounted to index metacarpal anchor 35, and index metacarpal anchor 35 and sling 45 are pre-mounted to driver 115 at the time of system assembly.

4. Driver 115 is used to place index metacarpal anchor 35 into bone hole 135 formed in index metacarpal 25.

5. Driver 115 is withdrawn from the deployed index metacarpal anchor 35, and thumb metacarpal anchor 40 is removably attached to driver 115 (or another driver).

6. The free end of sling 45 is secured to thumb metacarpal anchor 40 using sling-engaging element 75 of thumb metacarpal anchor 40 and adjustable anchor-engaging element 95 of sling 45. In one preferred form of the invention, this is effected by pulling second end 85 of sling 45 so as to decrease the diameter of loop 100, whereby to secure adjustable loop 100 to groove 75 of thumb metacarpal anchor 40 (i.e., to cinch loop 100 of sling 45 into groove 75 of index metacarpal anchor 40).

7. Thumb metacarpal anchor 40 is pulled towards index metacarpal 25 (e.g., as the diameter of adjustable loop 100 is decreased).

8. When thumb metacarpal anchor 40 has been advanced to the appropriate location, thumb metacarpal anchor 40 is inserted into the base of thumb metacarpal 15 while sling 45 is securely captured to thumb metacarpal anchor 40 (e.g., while adjustable loop 100 is securely captured in groove 75 of thumb metacarpal anchor 40). Note that insertion of thumb metacarpal anchor 35 into bone hole 140 in thumb metacarpal 15 captures adjustable anchor-engaging element 95 (e.g., loop 100) of sling 45 in bone hole 140 so that adjustable anchor-engaging element 95 cannot disengage from thumb metacarpal anchor 40 (a sling-to-anchor fixation). In addition, insertion of thumb metacarpal anchor 35 into bone hole 140 in thumb metacarpal 15 captures portions of sling 45 between thumb metacarpal anchor 40 and thumb metacarpal 15 with a binding interference fit (a binding interference fit between anchor and bone). This combination of sling fixations (i.e., the sling-to-anchor fixation and the binding interference fit between anchor and bone) leads to a very stable fixation of sling 45 to thumb metacarpal 15, and hence to the creation of a very stable suspension between index metacarpal 25 and thumb metacarpal 15.

9. Thumb metacarpal anchor 40 is inserted to a desired depth so as to complete the formation of a suspension sling between index metacarpal 25 and thumb metacarpal 15. This suspension sling, which extends from index metacarpal anchor 35 (which is secured in index metacarpal 25) to thumb metacarpal anchor 40 (which is secured in thumb metacarpal 15) is able to support the thumb of a patient after basal joint arthroplasty had been performed in order to alleviate basal joint arthritis. Note that thumb metacarpal anchor 40 can be also be inserted on the far side of thumb metacarpal 15 (i.e., the side facing away from index metacarpal 25), thereby enabling sling 45 to traverse the entire base of thumb metacarpal 15.

10. Second end 85 of sling 45 can then be cut with an appropriate instrument if desired.

Additional Constructions

Figure 6:
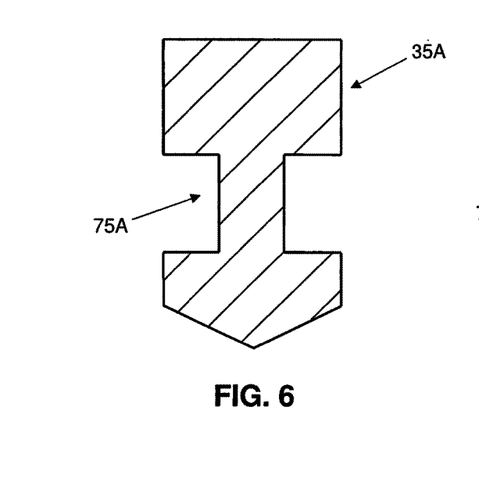
FIGS. 6-9 are schematic views showing alternative anchors which may be used in conjunction with the present invention.
Figure 7:
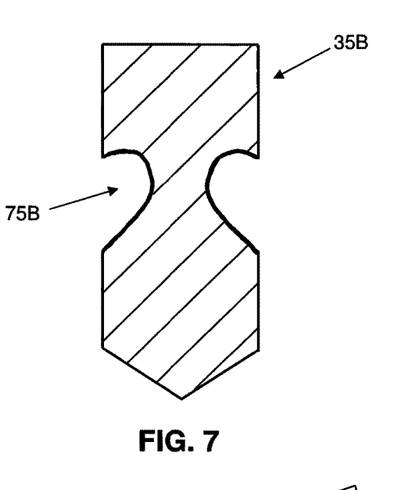
Figure 8:
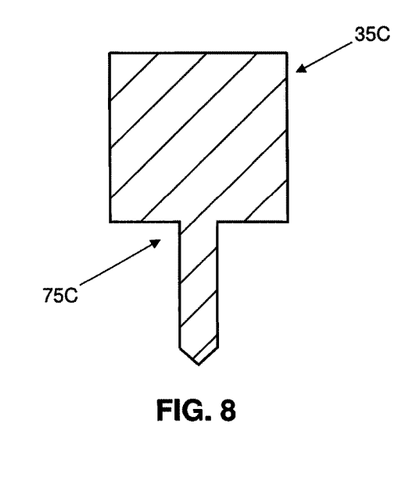
Figure 9:
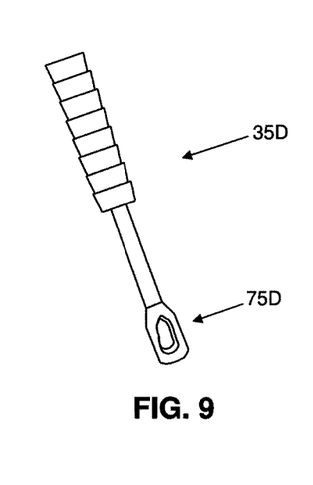

It is anticipated that index metacarpal anchor 35 and/or thumb metacarpal anchor 40 may be replaced by other sling anchors. By way of example but not limitation, thumb metacarpal anchor 40 may be replaced by the thumb metacarpal anchor 40A shown in FIG. 6, or by the thumb metacarpal anchor 40B shown in FIG. 7, or by the thumb metacarpal anchor 40C shown in FIG. 8. Furthermore, thumb metacarpal anchor 40 could be replaced by the thumb metacarpal anchor 40D shown in FIG. 9, which comprises the Pushlock™ suture anchor available from Arthrex, Inc. of Naples, Fla., USA. With an anchor of this type, sling 45 can omit the aforementioned adjustable loop 100, and the second (free) end of sling 45 can be passed through eyelet 75D formed in the anchor. In this form of the invention, sling 45 is captured to the bone by an interference fit between the body of the anchor and the bone.

It is also anticipated that index metacarpal anchor 35 and thumb metacarpal anchor 40 may be simultaneously loaded in the same driver, with index metacarpal anchor 35 being disposed distal to thumb metacarpal anchor 40.

Furthermore, it is also contemplated that, if desired, the adjustability of the sling suspension may be provided on the index metacarpal side of the sling suspension rather than on the thumb metacarpal side of the sling suspension. Thus, in this alternative form of the invention, index metacarpal anchor 35 would be set in thumb metacarpal 15, and thumb metacarpal anchor 40 would be set in index metacarpal 25, with the sling being tensioned on the index metacarpal side of the sling suspension.

In addition to the foregoing, it should also be appreciated that the present invention may be used in basal joint arthroplasties which may be conducted for purposes other than alleviating basal joint arthritis, e.g., such as in the case of disease and/or trauma.

MODIFICATIONS

It is to be understood that the present invention is by no means limited to the particular constructions herein disclosed and/or shown in the drawings, but also comprises any modifications or equivalents within the scope of the invention.

What is claimed is:

1. A method for supporting the thumb of a patient after basal joint arthroplasty, said method comprising:
    providing a system comprising an index metacarpal anchor, a thumb metacarpal anchor, and a sling connecting said thumb metacarpal anchor to said index metacarpal anchor,
        wherein said index metacarpal anchor comprises a body having at least one bone-engaging element for engaging the index metacarpal of a patient and a sling-engaging element for securing a first portion of said sling to said index metacarpal anchor,
        wherein said thumb metacarpal anchor comprises a body having at least one bone-engaging element for engaging the thumb metacarpal of a patient and a sling-engaging element for securing a second portion of said sling to said thumb metacarpal anchor, and
        wherein the length of said sling between said index metacarpal anchor and said thumb metacarpal anchor is adjustable;
    removing at least a portion of the trapezium of the patient so as to create a void at the base of the thumb metacarpal and so that the thumb metacarpal of the patient is no longer supported by the trapezium of the patient; and
    positioning said index metacarpal anchor in the index metacarpal of a patient so that said first portion of said sling is secured to said index metacarpal of said patient, and positioning said thumb metacarpal anchor in the thumb metacarpal of a patient so that said second portion of said sling is secured to said thumb metacarpal of said patient, with the length of the sling between said index metacarpal anchor and said thumb metacarpal anchor being adjusted such that said sling secures the thumb metacarpal to the index metacarpal, whereby to prevent the thumb metacarpal from occupying the void left by removal of at least a portion of the trapezium of the patient and thereby support the thumb of a patient after basal joint arthroplasty.

2. A method according to claim 1 wherein said at least one bone-engaging element of said index metacarpal anchor comprises one from the group consisting of a screw thread and a rib.

3. A method according to claim 1 wherein said sling-engaging element of said index metacarpal anchor comprises an eyelet.

4. A method according to claim 1 wherein said at least one bone-engaging element of said thumb metacarpal anchor comprises one from the group consisting of a screw thread and a rib.

5. A method according to claim 1 wherein said sling-engaging element of said thumb metacarpal anchor comprises a shoulder.

6. A method according to claim 5 wherein said shoulder comprises a portion of a groove.

7. A method according to claim 6 wherein said groove extends completely around said thumb metacarpal anchor.

8. A method according to claim 1 wherein said sling comprises a knot.

9. A method according to claim 1 wherein said sling comprises an adjustable loop.

10. A method according to claim 9 wherein said adjustable loop is formed by passing said sling through itself.

11. A method according to claim 9 wherein said adjustable loop is formed by a sliding knot.

12. A method according to claim 1 wherein said sling is in the form of a filament.

13. A method according to claim 12 wherein said filament is in the form of a suture.

14. A method according to claim 1 wherein said index metacarpal anchor is positioned in the side of the index metacarpal.

15. A method according to claim 1 wherein said index metacarpal anchor is positioned in the base of the index metacarpal.

16. A method according to claim 1 wherein said thumb metacarpal anchor is positioned in the base of the thumb metacarpal.

17. A method according to claim 1 wherein said thumb metacarpal anchor is positioned in the side of the thumb metacarpal.

18. A method according to claim 1 wherein said sling is fixedly secured to said index metacarpal anchor.

19. A method according to claim 1 wherein said sling is adjustably secured to said index metacarpal anchor.

20. A method according to claim 19 wherein the length of said sling between said index metacarpal anchor and said thumb metacarpal anchor is set before said index metacarpal anchor is positioned in the index metacarpal of the patient.

21. A method according to claim 20 wherein said thumb metacarpal anchor is positioned in the thumb metacarpal of the patient before said index metacarpal anchor is positioned in the index metacarpal of the patient.

22. A method according to claim 1 wherein said sling is fixedly secured to said thumb metacarpal anchor.

23. A method according to claim 1 wherein said sling is adjustably secured to said thumb metacarpal anchor.

24. A method according to claim 23 wherein the length of said sling between said index metacarpal anchor and said thumb metacarpal anchor is set before said thumb metacarpal anchor is positioned in the thumb metacarpal of the patient.

25. A method according to claim 24 wherein said index metacarpal anchor is positioned in the index metacarpal of the patient before said thumb metacarpal anchor is positioned in the thumb metacarpal of the patient.

26. A method for alleviating basal joint arthritis, said method comprising:

excising the trapezium of a patient so as to create a void at the base of the thumb metacarpal and so that the thumb metacarpal of the patient is no longer supported by the trapezium of the patient;

securing a first end of a sling to an index metacarpal anchor, wherein said index metacarpal anchor comprises a body having at least one bone-engaging element for engaging the index metacarpal of a patient and a sling-engaging element for securing said first end of said sling to said index metacarpal anchor;

positioning said index metacarpal anchor in the index metacarpal of a patient;

adjustably securing said second end of said sling to a thumb metacarpal anchor, wherein said thumb metacarpal anchor comprises a body having at least one bone-engaging element for engaging the thumb metacarpal of the patient and a sling-engaging element for adjustably securing said second end of said sling to said thumb metacarpal anchor;

adjusting the securement of said second end of said sling to said thumb metacarpal anchor so that said thumb metacarpal anchor is brought adjacent to the thumb metacarpal of the patient; and inserting said thumb metacarpal anchor into the thumb metacarpal of the patient so that said second end of said sling is fixedly secured to said thumb metacarpal anchor, whereby said sling fixedly connects the thumb metacarpal of the patient to the index metacarpal of the patient, with the length of said sling between said index metacarpal anchor and said thumb metacarpal anchor being sized such that said sling secures the thumb metacarpal to the index metacarpal, whereby to prevent the thumb metacarpal from occupying the void left by excising the trapezium of the patient and thereby support the thumb of a patient after basal joint arthroplasty.

* * * * *